United States Patent [19]

Fein et al.

[11] Patent Number: 5,440,385
[45] Date of Patent: Aug. 8, 1995

[54] INTEGRATED ISOTROPIC ILLUMINATION SOURCE FOR TRANSLUCENT ITEM INSPECTION

[75] Inventors: Howard Fein, Richmond Heights; Terry L. Graves, Wadsworth, both of Ohio

[73] Assignee: Pressco Technology, Inc., Solon, Ohio

[21] Appl. No.: 13,965

[22] Filed: Feb. 5, 1993

[51] Int. Cl.⁶ .............................. G01N 21/90
[52] U.S. Cl. .......................... 356/240; 250/223 B; 362/355
[58] Field of Search ............... 356/237–240, 356/138; 362/235, 260, 355, 363, 800, 255, 256; 250/223 B

[56] References Cited

U.S. PATENT DOCUMENTS

| | | | |
|---|---|---|---|
| 2,163,272 | 6/1939 | Deschere | 362/255 |
| 4,054,286 | 10/1977 | Dressler, Sr. | 362/355 |
| 4,882,498 | 11/1989 | Cochran et al. | 250/571 |
| 4,959,537 | 9/1990 | Kimoto et al. | 356/240 |
| 5,257,173 | 10/1993 | Ohmamyuda et al. | 362/800 |

*Primary Examiner*—Robert P. Limanek
*Assistant Examiner*—David B. Hardy
*Attorney, Agent, or Firm*—Fay, Sharpe, Beall, Fagan, Minnich & McKee

[57] ABSTRACT

A substantially isotropic illumination source utilizes a generally spherical, translucent diffuser. The spherical diffuser has an inner wall and a diffusive outer wall. Light is communicated inwardly to the sphere along a first hemisphere. Light is diffused and homogenized by internal reflection within the sphere and communicated outwardly through a complimentary hemisphere. This light, upon being diffused by the external or outer wall is substantially isotropic. The isotropic light so generated is utilized for video inspection of translucent specimens with improved contrast to facilitate detection of flaws therein. Another aspect utilizes a specimen itself as the isotropic diffuser.

20 Claims, 4 Drawing Sheets

INTEGRATED ISOTROPIC ILLUMINATION SOURCE FOR TRANSLUCENT ITEM INSPECTION

BACKGROUND OF THE INVENTION

The subject application pertains to the art of video inspection, and more particularly to improved illumination therefor implementing a highly integrated isotropic illumination emitter.

The invention is particularly applicable to providing improved, isotropic illumination for inspection of translucent or partially translucent materials or objects and will be described with particular reference thereto. However, it will also be appreciated that the invention has broader application, such as in providing illumination for any application in which isotropic light is advantageous.

Video inspection has become a well accepted and advantageous means of assuring quality control of manufactured product. Systems employing such inspection are particularly useful in connection with mass-produced items such as containers, including bottles, cans, and the like.

Early inspection system relied mainly on sophisticated, computation-intensive algorithms to accomplish inspection. In U.S. Pat. No. 4,882,498 owned by Pressco Technology, Inc., assignee hereof, the contents of which are incorporated herein by reference, an early understanding that significant improvements would be achieved by engineering lighting was provided. Manipulation and refinement of lighting techniques provides a cleaner, truer image from which the video inspection process may be commenced. This serves to minimize computation and algorithm complexity while simultaneously improving inspection throughput and integrity. The above-noted patent utilized solid-state light emitting diode illumination for its light generation. This invention acknowledged and facilitated improvements by providing easy manipulatable, highly-homogeneous lighting. While the resultant inspection improvement was marked, certain applications for video inspection would be even better realized with the provision of a more uniform, isotropic lighting. This is particularly true in connection with inspection of light transmissive or translucent specimens.

The present invention contemplates a new and improved illumination system particularly suited for video inspection which overcomes many of the above-referred problems, and others, and provides an isotropic illumination source which is simple, economical, and facilitates high integrity inspection. The present system teaches an improved, isotropic illumination source that defeats most prevalent total internal reflection effects associated with refraction shadowing in a transparent medium.

SUMMARY OF THE INVENTION

In accordance with the present invention, there is provided an illumination system employing a generally spherical translucent diffuser having a generally continuous inner wall portion and a generally continuous outer wall portion disposed radially outward from the inner wall portion. The diffuser is defined to include first and second complementary hemispheres. Light is received into a first hemisphere. Light so received is subject to combined internal reflection within the sphere and transmission through the walls thereof. At least an outer surface of the sphere is comprised of a diffusive form so as to scatter further light associated therefrom. Thus, a substantially isotropic illumination source is realized by illuminations emanating from the second or complementary hemisphere.

In accordance with another aspect of the present invention, light provided to the first hemisphere is generated by an array of solid-state light generating sources, such as light emitting diodes. In accordance with another aspect of the present invention, a video inspection system is provided which accomplishes video image acquisition of a specimen resultant from illumination of the specimen by the above system.

In accordance with yet another aspect of the invention, a method to accomplish isotropic illumination and video inspection in accordance with the foregoing is provided.

An advantage of the present invention is the provision of a system for generating improved, isotropic lighting.

Yet another advantage of the present invention is the provision of a video inspection system with increased integrity and fault detection capabilities relating to the isotropic lighting achieved and utilized.

Yet another advantage of the present invention is the provision of an isotropic illumination system which is engineered to enhance image contrast and defect detection.

Further advantages will be more fully appreciated by one of ordinary of skill in the art upon reading and understanding of the subject specification and drawings.

BRIEF DESCRIPTION OF THE DRAWINGS

This invention may take physical form in certain parts and arrangements of parts, the preferred embodiment of which will be described in detail in this specification and illustrated in the accompanying drawings which form a part hereof and wherein.

DETAILED DESCRIPTION OF THE PREFERRED EMBODIMENT

Figure 1:
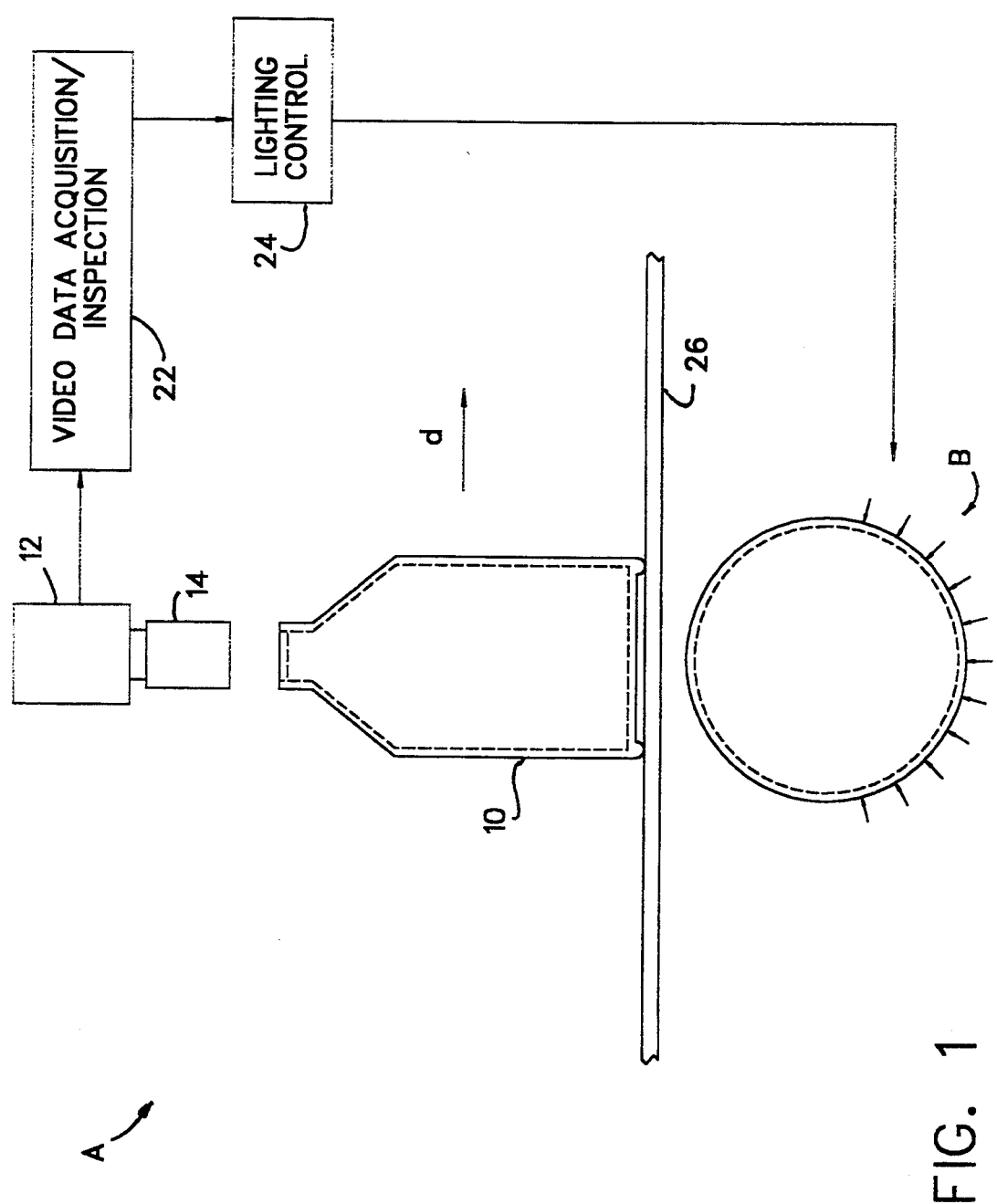
FIG. 1 illustrates a video inspection system employing the improved, isotropic lighting of the present invention.

Turning now to the figures wherein the illustrates are for the purpose of illustrating the preferred embodiment only, and not for the purpose of limiting the same, FIG. 1 illustrates and inspection system A which includes an isotropic illumination subsystem B. The increased isotropic properties eliminate "hot spots" deleterious to clean image acquisition. In the inspection system, an illustrative specimen 10 in a sequence or stream thereof moves in a direction d relative to illumination subsystem B and a video acquisition means, such as camera 12.

In the preferred embodiment, the camera 12 includes a lens 14 for focusing light received therein onto a charge coupled device ("CCD") array disposed within the camera 12. The particular embodiment evidences a light transmissive or translusive specimen or specimen portion as forming the specimen 10. The illumination subsystem B is disposed opposite the specimen 10 of the camera 12. In this way, direct or transmissive lighting of the specimen is accomplished for inspection purposes. However, it will be appreciated, specular illumination is also achievable with isotropic lighting.

Light generated from the illumination subsystem B accordingly passes to a viewing area indicated generally at 20. More particularly, the viewing area 20 is defined as the area conducive to specimen illumination by the subsystem B, for acquisition of an image by the camera 12 and lens 14.

A planar, pixel-based image acquired by camera 12 includes gray scale information relating to the brightness level associated with each of such pixels. This information is communicated to video data acquisition-/inspection system 22 for computation, comparison, and analysis as will be appreciated by one of ordinary skill in the art.

The intelligence associated with the video data acquisition/inspection system 22 directs a lighting control 24. The lighting control is suitably that available with conventional systems and provides for control of lighting intensity, duration, and light array manipulation in lighting embodiment including such an array. Particulars of the lighting array of the preferred embodiment will be detailed below.

Each of the specimens such as that 10 in the illustration are sequentially communicated to the viewing area 20 by a suitable means such as that illustrated by belt 26. The belt 26 is suitably transparent or apertured to facilitate illumination therethrough. It will also be appreciated that the belt 26 may be formed so as to secure specimens such as that from a side or sides thereof so as not to obscure illumination and image acquisition.

Figure 2:
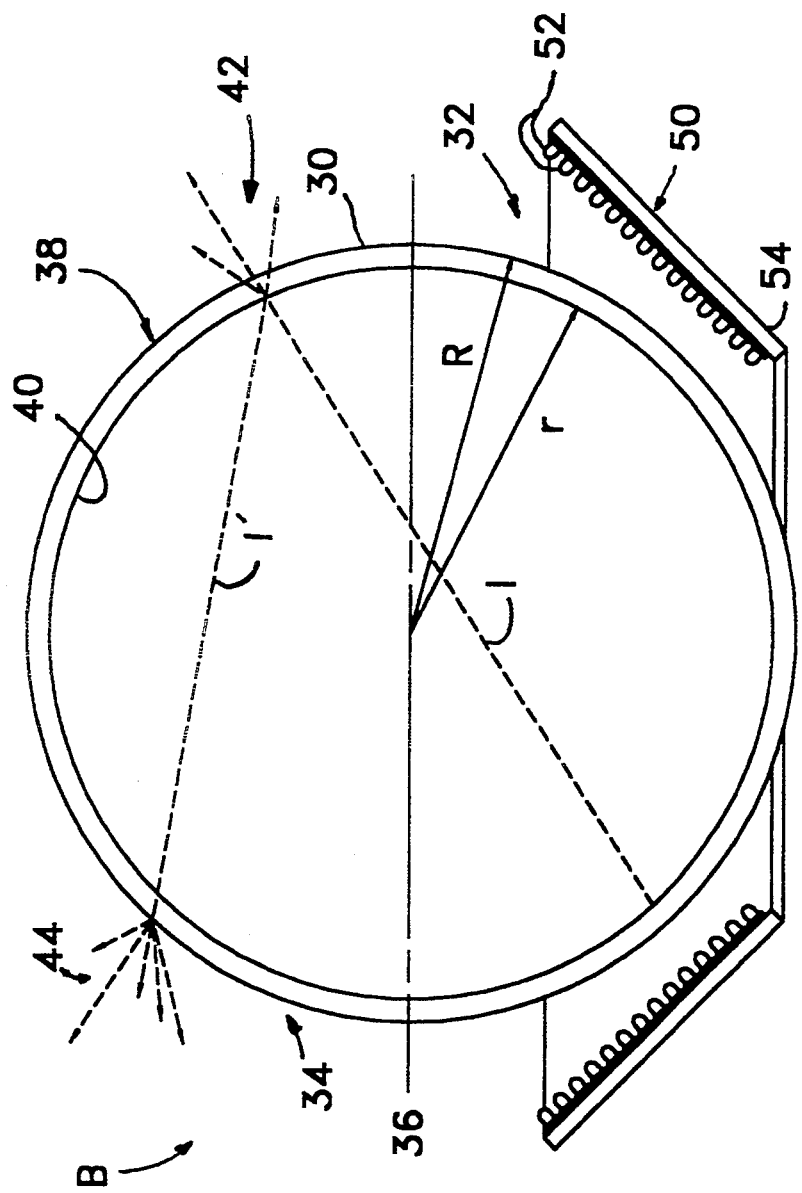
FIG. 2 illustrates a cross-section of an embodiment of an isotropic light generator as illustrated in FIG. 1.

Turning now to FIG. 2, a cut-away view, in greater detail, of the isotropic illumination subsystem B is provided. Illustrated in the cross-section is a division of a generally spherical diffuser 30 into a first hemisphere 32 and a second hemisphere 34. The division is taken from a centerline illustrated at 36.

In the illustration, the sphere 30 has an exterior radius R and an internal radius r. Thus, the thickness of the sphere is R−r. It will be appreciated that the exterior surface area of the sphere is therefore $4\pi R^2$. Further, an internal surface area is $4\pi r^2$. In the preferred embodiment, the cavity defined by the internal wall 40 contains air, which contents provide the advantages of the subject system. However, any substance, even a solid sphere, provides improved illumination isotropism.

The sphere 30 is suitably formed from any light transmissive or translucent material such as glass or plastic. An exterior surface 38 of the sphere 30 is selected to provide light scattering or dispersion as it passes from the sphere 30 to the surrounding medium. A representative light ray 1 is illustrated as propagating through an interior of sphere 30 to an inner wall or surface 40.

A portion of the light 1 incident on the inner wall 40 will be reflected at an angle of incidence to a tangent to the inner wall equal to an angle of reflection therefrom. Such internally reflected light is illustrated at 1'. It will be seen that a portion of the light is also passed through this sphere 30 and scattered therefrom as illustrated generally at 42. The particulars of the light transmission and scattering will be detailed below in connection with FIG. 3. Similarly, a portion of the light internally reflected at 1' will be scattered as illustrated at 44.

FIG. 2 also illustrates a light source 50. Light source 50 provides illumination to sphere 30 at the first hemisphere 32. In this fashion, light thus received may be internally reflected and passed and diffused so as to illuminate a specimen by passing outwardly through the second hemisphere portion 34 of sphere 30. It is to be appreciated that merely wrapping a light source with a diffuser does not provide the subject advantages. Such light still appears directional in nature causing self-lensing properties of a medium to display internal reflection "shadows."

In the preferred embodiment, the light source 50 is comprised of an array of directed light emitting diodes 52 secured by a mounting bracket or means 54. In the illustration, the mounting bracket 54 secures the LEDs 52 in a general frustoconical form. This form advantageously provides for substantial lighting and maximizes the utilization of the isotropic rendering accomplished by the sphere 30. LEDs provide relative long life and ease in controllability as will be appreciated. Further, utilization of a large number of LEDs in the array provides improved lighting homogeneity which is augmented by utilization of the disclosed spherical diffuser. While LEDs are advantageously employed, it will be appreciated that such lighting may be suitably accomplished by any light having sufficient intensity, such an incandescent, fluorescent, halide, arc, or the like.

Figure 3:
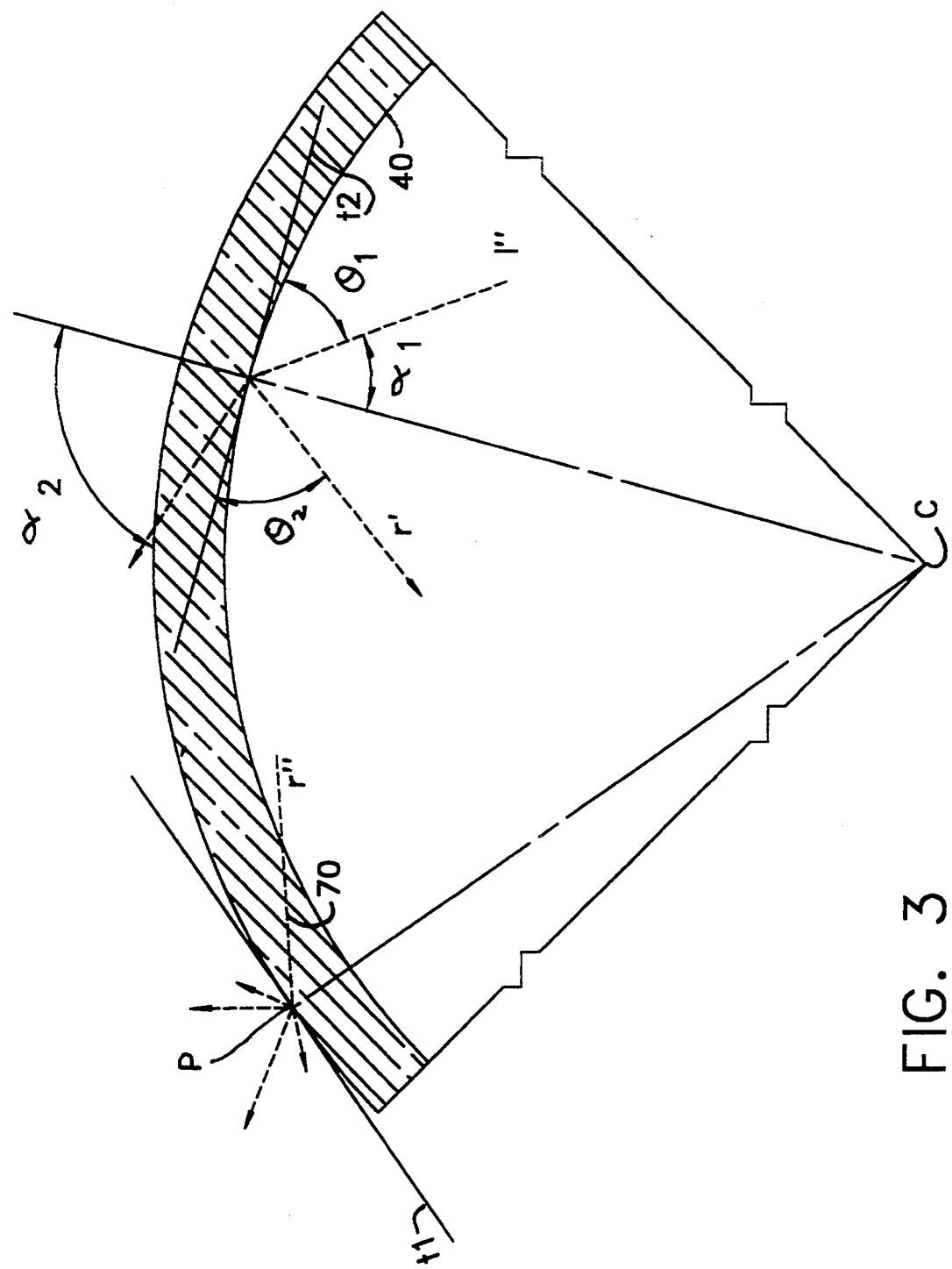
FIG. 3 illustrates a cross-sectional, cut-away view of the light generator of FIGS. 1 and 2.

Turning now to FIG. 3, a cross-sectional portion of the cut-away of FIG. 2 is described. Therein, a center point C is illustrated for the sphere 30. Perpendicular to each point on a radius from the center point C to the inner wall 40 is a tangent, one of which is illustrated at t2. An illustrated light array 1" is travelling within the center of the sphere 30. As it impacts the transition between the internal sphere portion and the inner wall 40, it experiences a difference between relative indices of refraction therebetween. A portion will be reflected by a property of total internal reflection and propagated within the sphere as r'. In this case, angle of incidence $\theta_1$, equals angle of reflection $\eta_2$. A portion of 1" will be transmitted at a modified angle as a beam r''. The angle of r'' relative to the tangent t2 is dictated by Snell's law. This law provides that the ratio between the sine of the angle of incident $\alpha_1$ to a tangent normal or line perpendicular to the boundary between the mediums at the point of refraction, to the sine of the angle $\alpha_2$ between r'' and the normal is equal to the ratio of the refracting medium's index of refraction $n_r$ to the original medium's index of refraction $n_i$.

Illustrated generally at 70 is a beam such as that r'' which has been propagated into the sphere body. At the point it reaches the transition with the exterior at the wall 30, evidenced as point p, additional refraction is experienced, coupled with diffusion from a diffusive coating or etching thereon. It is to be appreciated that such diffusive properties may suitably be additionally imparted on the inner wall 40, or dispersed within the material forming the sphere itself. However, the advantages of the subject invention are realized when the diffusion properties on the external wall 30 are provided.

With the foregoing, it will be appreciated that relatively intense beams of light are subject to separation via internal reflection, refraction, and deflection scattering. Thus, the sphere provides for accomplishing generation of homogenous or isotropic light generation. Further, the specimen itself is not illuminated directly from any source other than the sphere. Thus, contrast enhancement and defect detection is enhanced. Evidence indicates that contrast is improved from 50% to 200% over systems employing flat planar illumination.

As an alternative embodiment to the foregoing, the light source 50 may be formed from an ultraviolet ("UV") source, such as an uncoated fluorescent bulb or xenon strobe. The diffusion coating is suitably formed from a coating which alters the UV wavelength to a selected spectrum. Such coatings are well understood and conventionally available.

Figure 4:
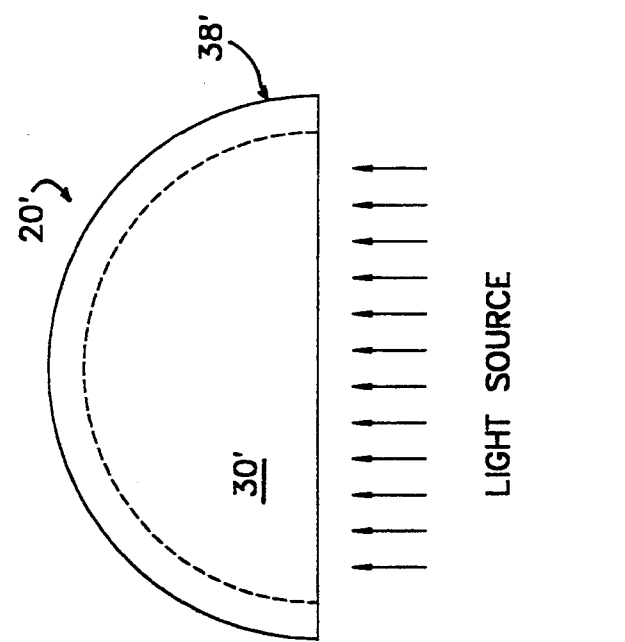
FIG. 4 illustrates an embodiment of the diffuser mechanism employing a hemispherical diffuser shape.

Turning now to FIG. 4, an embodiment wherein a hemispherical diffuser 30' is implemented is disclosed. Therein, a light source, suitably planar, structured array, or even point source, is directed to an interior of the hemisphere 30'. The specimen is suitably disposed in the viewing area located on the curved side of the hemisphere 30' indicated generally at 20'. As with the above-described full sphere, the hemisphere 30' is adapted for either transmissive or specular illumination of specimens with highly isotropic light. Again, as with the sphere 30, above, the isotropic light generated by the hemisphere 30' is realizable by either a structured, planar light source, a narrow beam, or a point source since the dispersion realized from the spherical portion and the diffusive properties of the exterior surface thereof accomplish such.

Figure 5:
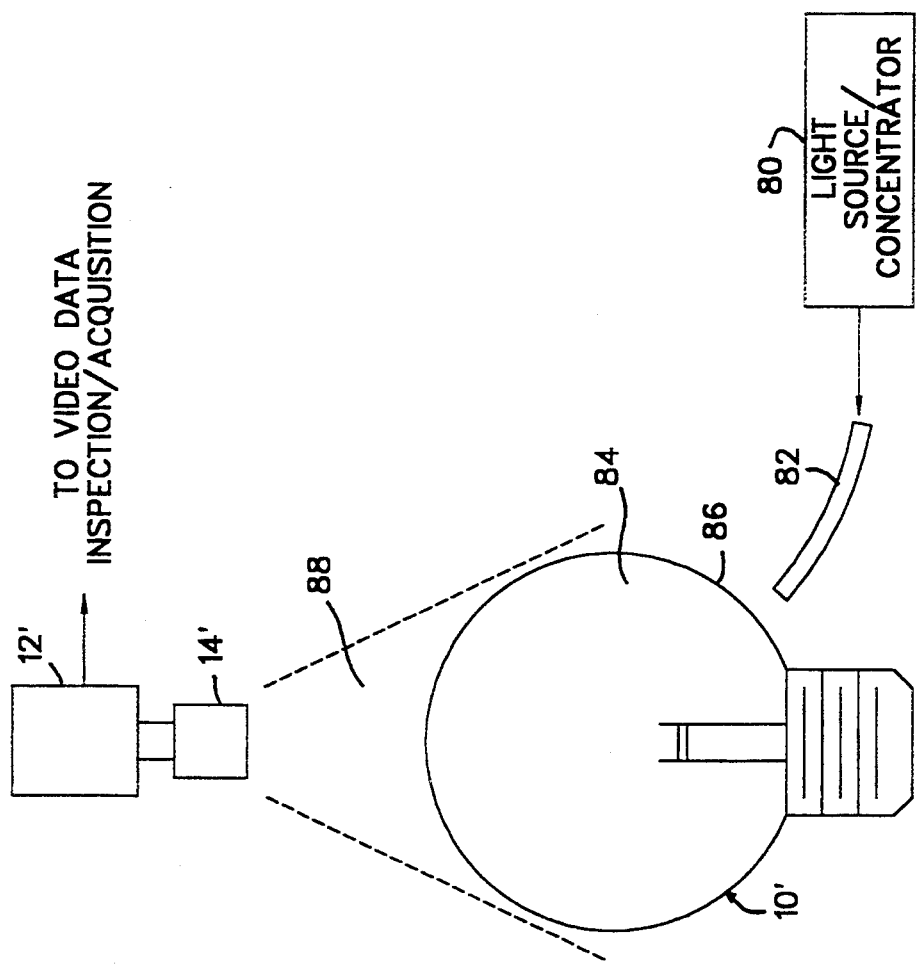
FIG. 5 illustrates an embodiment wherein the specimen itself accomplishes the isotropic light generation for use in video inspection.

Turning now to FIG. 5, an embodiment wherein a specimen itself functions to create an isotropic light field is illustrated. Therein, the specimen 10' is illustrated as an incandescent light bulb. A light source 80, which may include a concentrator in this embodiment, communicates light to a light pipe 82. Light pipe 82 is suitably comprised of a light wave guide, such as a fiber optic cable. The light pipe 82 communicates light to a basal hemisphere portion of the specimen 10'. Light communicated internally to the globe portion 84 of the specimen 10' is rendered substantially isotropic by the spherical portion thereof, coupled with a coating on an effective surface 86 of the portion 84.

A substantially spherical portion of surface 84 is exposed to a field of view 88 of lens 14' and camera 12', as was described above. With this rendering, a means for highly efficient and reliable inspection for flaws disposed within objects such as that 10' is facilitated.

The invention has been described with reference to the preferred embodiment. Obviously, modifications and alternations will occur to others upon a reading and understanding of this specification. It is intended that all such modifications and alterations be included insofar as they come within the scope of the appended claims or the equivalents thereof.

Having thus described the invention, it is now claimed:

1. A substantially isotropic video inspection illumination system comprising:
   a generally translucent ellipsoid like diffuser having an imperforate inner wall portion and an imperforate outer wall portion disposed radially outward from the inner wall portion, the diffuser including first and second hemi-ellipsoid like portions;
   means adapted for receiving light, through the first hemi-ellipsoid like portion from an exterior portion thereof, into an interior of the diffuser contained by the inner wall portion;
   means adapted for communicating isotropic light from an interior of the second hemi-ellipsoid like portion to an associated specimen for illumination thereof, such that the associated specimen is illuminated by diffuse, multi-directional light;
   means for acquiring an image of each specimen after illumination thereof by the diffuse, multi-directional light; and
   means for determining acceptability of each specimen in accordance with an acquired image corresponding thereto.

2. The video inspection illumination system of claim 1 wherein the inner wall is substantially transparent and wherein the outer wall defines a diffusive surface.

3. The video inspection illumination system of claim 2 wherein light communicated to the first hemi-ellipsoid like portion is in a narrow beam.

4. The video inspection illumination system of claim 2 further comprising a light generator for generating the light communicated to the first hemi-ellipsoid like portion.

5. The video inspection illumination system of claim 4 wherein the light generator is comprised of a solid-state light source.

6. The video inspection illumination system of claim 1 wherein the generally translucent diffuser is formed from a translucent material having an exterior, diffusive surface.

7. The video inspection illumination system of claim 6 wherein the associated specimen is comprised of translucent material whereby transmissive lighting is affected thereon.

8. The video inspection illumination system of claim 7 further comprising:
   a light generator comprised of a directed array of light emitting diodes; and
   means for securing the array of light emitting diodes in a generally frusto-conical array such that the light therefrom is generally directed at the first ellipsoidal portion.

9. A substantially isotropic video inspection illumination system comprising:
   a generally translucent diffuser having an imperforate, substantially transparent inner wall portion and an imperforate outer wall portion that defines a diffusive surface disposed radially outward from the inner wall portion, the diffuser including at least one hemisphere;
   means adapted for receiving light internally to the diffuser by passage of light therethrough;
   means adapted for communicating light from an interior of the at least one hemisphere to an associated specimen for illumination thereof, whereby the associated specimen is illuminated by diffuse, multi-directional light;
   a light generator for generating the light communicated to a second hemisphere, wherein the light generator is further comprised of a directed array of solid state light emitting diodes;
   means for acquiring an image of each specimen after illumination thereof by the diffuse, multi-directional light; and
   means for determining acceptability of each specimen in accordance with an acquired image corresponding thereto.

10. The video inspection illumination system of claim 9 wherein the light generator includes means for securing the array of light emitting diodes in a generally frusto-conical array such that the light therefrom is generally directed at the second hemisphere similar to the at least one hemisphere.

11. A method of generating substantially isotropic video inspection illumination comprising the steps of:

receiving input light through an exterior of a first hemi-ellipsoid like portion of an ellipsoid like translucent diffuser having an imperforate inner wall portion and an imperforate outer wall portion disposed radially outward from the inner wall portion, the diffuser including the first hemi-ellipsoid like portion and a second hemi-ellipsoid like portion similar to the first hemi-ellipsoid like portion;

communicating substantially isotropic light through the second second hemi-ellipsoid like portion to an associated specimen for illumination thereof, such that the associated specimen is illuminated by diffuse, multi-directional light;

means for acquiring an image of each specimen after illumination thereof by the diffuse, multi-directional light; and means for determining acceptability of each specimen in accordance with an acquired image corresponding thereto.

12. The method of claim 11 wherein the step of receiving light includes receiving the input light into the outer wall portion of the generally spherical translucent diffuser wherein the inner wall is substantially transparent and wherein the outer wall defines a diffusive surface.

13. The method of claim 12 wherein the step of receiving light further includes receiving a narrow light beam into the generally spherical translucent diffuser.

14. The method of claim 12 further comprising a step of generating the input light communicated to the second hemisphere.

15. The method of claim 14 wherein the step of generating the light includes the step of generating the input light from a solid-state light source.

16. The method of claim 15 wherein the step of generating the light further includes the step of generating the input light from the solid-state light source formed from a directed array of light emitting diodes.

17. A video inspection system comprising:

means for sequentially communicating a stream of specimens to a viewing area;

a generally spherical translucent diffuser having an imperforate inner wall portion and an imperforate outer wall portion disposed radially outward from the inner wall portion, the diffuser including first and second similar hemispheres;

a light generator for generating light communicated to the second hemisphere;

means adapted for receiving light from the light generator the first hemisphere of the diffuser;

means for communicating light from the second hemisphere to the viewing area for illumination thereof, whereby the associated specimen is illuminated by generally isotropic light;

means for acquiring an image of each specimen of a sequence thereof disposed in the viewing area, which image is acquired with illumination of the specimen by the generally isotropic light; and means for determining acceptability of each specimen of the sequence in accordance with an acquired image corresponding thereto.

18. The video inspection illumination system of claim 17 wherein the light generator is comprised of a solid-state light source.

19. The video inspection illumination system of claim 18 wherein the inner wall is substantially transparent and wherein the outer wall defines a diffusive surface.

20. The video inspection illumination system of claim 19 wherein each specimen of the stream is comprised of translucent material.

* * * * *